United States Patent [19]
Karayiorgou et al.

[11] Patent Number: 5,863,734
[45] Date of Patent: Jan. 26, 1999

[54] METHOD OF TREATMENT FOR OBSESSIVE-COMPULSIVE DISORDER

[75] Inventors: Maria Karayiorgou; Joseph A. Gogos, both of New York, N.Y.

[73] Assignee: The Rockfeller University, New York, N.Y.

[21] Appl. No.: 790,374

[22] Filed: Jan. 28, 1997

[51] Int. Cl.$^6$ .............................. C12Q 1/68; C12P 19/34; C07H 21/04; C12N 15/00

[52] U.S. Cl. ........................ 435/6; 435/91.1; 435/91.2; 435/810; 536/23.1; 536/24.33; 935/76; 935/77; 935/78

[58] Field of Search .............................. 435/6, 91.1, 91.2, 435/183, 810; 536/23.1, 24.31, 24.33

[56] References Cited

PUBLICATIONS

Balthazart et al., J. Steroid Biochem. Mol. Biol. 56, 185–200 (1996).
Bower, B. (1997) Science News 151:269.
Cohn et al. Life Sci. 10, 1351–1354 (1971).
Karayiorgou et al., Proc. Natl. Acad. Sci. USA 92, 7612–7616 (1995).
Karayiorgou, M. et al. (1996) Genotype and Phenotype Analysis at the 22q11 Schizophrenia Susceptibility Locus, Cold Spring Harbor Symposia on Quantitative Biology, vol. LXI, pp. 835–843, CSHL Press, Cold Spring Harbor, New York.
Karayiorgou et al. (1997) Proc. Natl. Acad. Sci. USA 94–4572–5.
Lachman et al. Pharmacogenetics 6, 243–250 (1996) (Medline Abst.).
Ladosky et al. Br. J. Med. Biol. Res. 14, 409–413 (1981) (Medline Abst.).
Lundstrom et al. (1991) DNA & Cell Biol. 10:181–9.
McDougle et al., J. Clin. Psych. 55 Suppl, 24–31 (1994).
Pauls et al. (1995) Am. J. Psychiatry 152:76–84.
Pulver, A.E. et al., J. Nerv. Mental Disease 182, 476–478 (1994).
Rasmussen et al. (1992) Psychiat. Clin. North Am. 15:743–59.
Vldgren et al. (1994) Nature 368:354–8.
Weinshilboum et al. Am. J. Hum. Genet. 29, 125–135 (1977).

*Primary Examiner*—Bradley L. Sisson
*Attorney, Agent, or Firm*—Klauber & Jackson

[57] ABSTRACT

Methods of identifying patients having a susceptibility to obsessive-compulsive disorder resultant from a reduced level of Catechol-O-methyltransferase (COMT) are described. Therapies, utilizing COMT or COMT agonists, or dopamine antagonists in combination therewith, are also envisioned, as well as methods for determining the patients which will benefit the most from such therapies.

5 Claims, 2 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3651 base pairs
        ( B ) TYPE: nucleic acid
        ( C ) STRANDEDNESS: double
        ( D ) TOPOLOGY: linear     ( i i ) MOLECULE TYPE: cDNA     ( i i i ) HYPOTHETICAL: NO     ( x i ) SEQUENCE DESCRIPTION: SEQ ID NO:1:

```
AGTATTGCTG  TTCAGATAGC  CTTTATTTGG  GTATATATTC  TACACTGTTT  TTAAATATGG      60

AGAGTAACCA  AAATGGCCCA  TTATCTGACC  ACACAAATAC  TAGTAGTCAT  TATAGATAAA     120

CCATAGCAGA  TAAATAATAG  TAAACAAAGC  AACAGGCTGT  GTCATTGGAA  ATCCCACCA      180

TGAAGAAAGG  AGCAAGGTGA  AAACTTCTGG  CTGCTTCAGG  TCATGCATGG  TCCCTCTCCA     240

CCATCGTTCC  CCCTGTCATC  TTCCTGCCAG  AATAAGGACC  CTGGTACCTT  AGGGAAGCAC     300

CATCTCTTGT  TTTTTCCCCA  CGAGCCCTGT  GGGTCATGGC  ACGTCCTGCC  CCGCTGGGAA     360

AACACAGTGG  GCCACGGGTT  TCCCTGCAGG  CCTGGACCCT  TCCCAAGGGT  AGCAGCAGAA     420

GGCAGCACGA  TTCCCACTCC  TGCAGCTGTG  ACAGGGCACC  CCCACTGTCA  CTGAGCCCTG     480

CACCGGGTTC  CATCACCTGC  TCGGGGCTCT  GCCTTTGGCC  TTTTCCTGTG  AACTGCATGT     540
```

| | | | | | |
|---|---|---|---|---|---|
| TGGCCACTGT | ACCTATCTGT | CTCTCATCTT | TTTTTCTTAC | GGGTTTGGGT | ATGTTCTTGG | 600 |
| TAAACCAGCC | CTTGGTCTTA | CACATCATTT | CCAAGGTACT | AAGGACTCTT | CAGGGGAAAT | 660 |
| ACAACTTGAG | CAGAGTGGTT | CCCTCCTCTT | GTGGTTCACA | AGGTGCAGGT | GCACACACAC | 720 |
| ATACCACAGG | GCAGTGTGAC | AGGACCAGAG | ACTGCCCCTG | GGGTCCCTGG | CTGGGGGACA | 780 |
| CTAGTAGGGA | TGTCCCTTGC | CTCTCTGAGG | CCTTCTGCTG | TCTCTTCTGA | GGCCGGAAAG | 840 |
| GCGAAGCACT | GCCCTCGCCC | TGCTAGGGAA | GGCTCAGGCC | AGGCTGGCCC | TATCCGGGGA | 900 |
| AGGGGCTCAG | GTATCTGGAC | CTTGGTCATC | GCCAGGTTAG | GGTTTATGTT | GATGATTATC | 960 |
| CAAAGGCAAA | ATTGATTTCC | ACAGAAATAA | CATCTGCTTT | GCTGCCGAGC | CAGAGGAGAC | 1020 |
| CCCAGACCCC | TCCCGCAGCC | AGAGGGCTGG | AGCCTGCTCA | GAGGTGCTTT | GAAGGTGAGT | 1080 |
| TGGCCAACGG | AAGCCGGGGC | AGTGCCAGGG | TGGACAGAA | GAGGCACACA | CCTGCTCTGT | 1140 |
| CTACCCGAGG | GCACCAGAGG | GCACGAGAAG | GCTGGCTCCC | TGGCGCTGAC | ACGTCAGGCA | 1200 |
| ACTGAGGCAC | AAGGCTGGCA | TTTCTGAACC | TTGCCCCTCT | GCGAACACAA | GGGGGCGATG | 1260 |
| GTGGCACTCC | AAGCAAAGGG | GCGTGTGGGT | GCTGCAGGAG | GAGCACAGAG | CACTGGCGCC | 1320 |
| CCTCCCCTCC | CGCCCTGCAG | ATGCCGGAGG | CCCCGCCTCT | GCTGTTGGCA | GCTGTGTTGC | 1380 |
| TGGGCCTGGT | GCTGCTGGTG | GTGCTGCTGC | TGCTTCTGAG | GCACTGGGGC | TGGGGCCTGT | 1440 |
| GCCTTATCGG | CTGGAACGAG | TTCATCCTGC | AGCCCATCCA | CAACCTGCTC | ATGGGTGACA | 1500 |
| CCAAGGAGCA | GCGCATCCTG | AACCACGTGC | TGCAGCATGC | GGAGCCCGGG | AACGCACAGA | 1560 |
| GCGTGCTGGA | GGCCATTGAC | ACCTACTGCG | AGCAGAAGGA | GTGGGCCATG | AACGTGGGCG | 1620 |
| ACAAGAAAGG | TTGGGGTTCC | GGGCCAGCAG | GTGCTCAGCT | CTGGGACAGG | GACCCAGGAC | 1680 |
| CAGGCATCAA | ATCCCGTGCC | TGGGGATCCA | AGTTCCCCTC | TCTCCACCTG | TGCTCACCTC | 1740 |
| TCCTCCGTCC | CCAACCCTGC | ACAGGCAAGA | TCGTGGACGC | CGTGATTCAG | GAGCACCAGC | 1800 |
| CCTCCGTGCT | GCTGGAGCTG | GGGGCCTACT | GTGGCTACTC | AGCTGTGCGC | ATGGCCCGCC | 1860 |
| TGCTGTCACC | AGGGGCGAGG | CTCATCACCA | TCGAGATCAA | CCCCGACTGT | GCCGCCATCA | 1920 |
| CCCAGCGGAT | GGTGGATTTC | GCTGGCGTGA | AGGACAAGGT | GTGCATGCCT | GACCCGTTGT | 1980 |
| CAGACCTGGA | AAAAGGGCCG | GCTGTGGGCA | GGGCGGGCAT | GCGCACTTTG | ATCCTCCCCA | 2040 |
| CCAGGTGTTC | ACACCACGTT | CACTGAAAAC | CCACTATCAC | CAGGGTCATC | CCAGAACCCT | 2100 |
| AAAGAAAACT | GATGAATGCT | TGTATGGGTG | TGTAAAGATG | GCCTCCTGTC | TGTGTGGGCG | 2160 |
| TGGGCACTGA | CAGGCGCTGT | TGTATAGGTG | TGTAGGGATG | GCCTCCTGTC | TGTGAGGACG | 2220 |
| TGGGCACTGA | CAGGCGCTGT | TCCAGGTCAC | CCTTGTGGTT | GGAGCGTCCC | AGGACATCAT | 2280 |
| CCCCCAGCTG | AAGAAGAAGT | ATGATGTGGA | CACACTGGAC | ATGGTCTTCC | TCGACCACTG | 2340 |
| GAAGGACCGG | TACCTGCCGG | ACACGCTTCT | CTTGGAGGTG | AGCCCCAACC | AGGATGGCAT | 2400 |
| CCGTGCCAGC | TGCTGCCCAG | AGCCCATTCA | GTCAGCCTCA | GCCTCTCCAA | AGAGCCAGGC | 2460 |
| ATTCCAGTAG | AGCCCTGTGT | GGACACAGCT | CGCTCTGGAG | GCACCACCTG | AGGTCTGGGA | 2520 |
| GTGTGGGGGA | CTGAGGAGGC | CCTGTGGTGG | GTGGAGATGG | GTGGGGAGCT | GGGCCAGGGG | 2580 |
| CTGGCTGGGT | GGCCTGTTGG | GAACTGGGGA | GCCAAGCGGT | CCCTGTCCTC | ACGGGCCCA | 2640 |
| TGTTCTGAAG | GTGGCACCCA | AGTCTTGTAC | AGTCCTTTCC | TGCAGGAGTC | ACGCTGGGCA | 2700 |
| GGAAGTGGAA | ACCTGGCCCC | AGGGGCTAGG | CACAGGCAGT | GGTGCCGTGG | CCTAGTGAGG | 2760 |
| AGCACCCATC | CTGGTTTGGG | GCAGGTTCTC | TGGGCACCTC | TGACCTCTCA | CCTCCCCAC | 2820 |
| CCCCCGGTCT | GTTTGCAGGA | ATGTGGCCTG | CTGCGGAAGG | GGACAGTGCT | ACTGGCTGAC | 2880 |
| AACGTGATCT | GCCCAGGTGC | GCCAGACTTC | CTAGCACACG | TGCGCGGGAG | CAGCTGCTTT | 2940 |

```
GAGTGCACAC ACTACCAATC GTTCCTGGAA TACAGGGAGG TGGTGGACGG CCTGGAGAAG    3000

GCCATCTACA AGGGCCCAGG CAGCGAAGCA GGGCCCTGAC TGCCCCCCCG GCCCCCCTCT    3060

CGGGCTCTCT CACCCAGCCT GGTACTGAAG GTGCCAGACG TGCTCCTGCT GACCTTCTGC    3120

GGCTCCGGGC TGTGTCCTAA ATGCAAAGCA CACCTCGGCC GAGGCCTGCG CCCTGACATG    3180

CTAACCTCTC TGAACTGCAA CACTGGATTG TTCTTTTTTA AGACTCAATC ATGACTTCTT    3240

TACTAACACT GGCTAGCTAT ATTATCTTAT ATACTAATAT CATGTTTTAA AAATATAAAA    3300

TAGAAATTAA GAATCTAAAT ATTTAGATAT AACTCGACTT AGTACATCCT TCTCAACTGC    3360

CATTCCCCTG CTGCCCTTGA CTTGGGCACC AAACATTCAA AGCTCCCCTT GACGGACGCT    3420

AACGCTAAGG GCGGGGCCCT AGCTGGCTGG GTTCTGGGTG GCACGCCTGG CCCACTGGCC    3480

TCCCAGCCAC AGTGGTGCAG AGGTCAGCCC TCCTGCAGCT AGGCCAGGGG CACCTGTTAG    3540

CCCCATGGGG ACGACTGCCG GCCTGGGAAA CGAAGAGGAG TCAGCCAAGC ATTCACACCT    3600

TTCTGACCAA GCAGGCGCTG GGACAGGTG GACCCGCAGC AGCACCAGCC C              3651
```

( 2 ) INFORMATION FOR SEQ ID NO:2:

( i ) SEQUENCE CHARACTERISTICS:
    ( A ) LENGTH: 271 amino acids
    ( B ) TYPE: amino acid
    ( C ) STRANDEDNESS: single
    ( D ) TOPOLOGY: linear ( i i ) MOLECULE TYPE: protein ( i i i ) HYPOTHETICAL: NO ( x i ) SEQUENCE DESCRIPTION: SEQ ID NO:2:

```
Met Pro Glu Ala Pro Pro Leu Leu Leu Ala Ala Val Leu Leu Gly Leu
 1               5                  10                  15

Val Leu Leu Val Val Leu Leu Leu Leu Arg His Trp Gly Trp Gly
                20                  25                  30

Leu Cys Leu Ile Gly Trp Asn Glu Phe Ile Leu Gln Pro Ile His Asn
            35                  40                  45

Leu Leu Met Gly Asp Thr Lys Glu Gln Arg Ile Leu Asn His Val Leu
        50                  55                  60

Gln His Ala Glu Pro Gly Asn Ala Gln Ser Val Leu Glu Ala Ile Asp
65                  70                  75                  80

Thr Tyr Cys Glu Gln Lys Glu Trp Ala Met Asn Val Gly Asp Lys Lys
                85                  90                  95

Gly Lys Ile Val Asp Ala Val Ile Gln Glu His Gln Pro Ser Val Leu
                   100                 105                 110

Leu Glu Leu Gly Ala Tyr Cys Gly Tyr Ser Ala Val Arg Met Ala Arg
            115                 120                 125

Leu Leu Ser Pro Gly Ala Arg Leu Ile Thr Ile Glu Ile Asn Pro Asp
        130                 135                 140

Cys Ala Ala Ile Thr Gln Arg Met Val Asp Phe Ala Gly Xaa Lys Asp
145                 150                 155                 160

Lys Val Thr Leu Val Val Gly Ala Ser Gln Asp Ile Ile Pro Gln Leu
                   165                 170                 175

Lys Lys Lys Tyr Asp Val Asp Thr Leu Asp Met Val Phe Leu Asp His
            180                 185                 190

Trp Lys Asp Arg Tyr Leu Pro Asp Thr Leu Leu Leu Glu Glu Cys Gly
        195                 200                 205

Leu Leu Arg Lys Gly Thr Val Leu Leu Ala Asp Asn Val Ile Cys Pro
```

```
            210                      215                           220
    Gly Ala Pro Asp Phe Leu Ala His Val Arg Gly Ser Ser Cys Phe Glu
    225                 230                 235                     240

Cys Thr His Tyr Gln Ser Phe Leu Glu Tyr Arg Glu Val Val Asp Gly
                    245                 250                 255

Leu Glu Lys Ala Ile Tyr Lys Gly Pro Gly Ser Glu Ala Gly Pro
                260                 265                 270
```

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PRIMER"

( i i i ) HYPOTHETICAL: NO

( x i ) SEQUENCE DESCRIPTION: SEQ ID NO:3:

```
TCACCATCGA GATCAACCCC                                                    20
```

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear     ( i i ) MOLECULE TYPE: other nucleic acid
        ( A ) DESCRIPTION: /desc = "PRIMER"

( i i i ) HYPOTHETICAL: NO

( x i ) SEQUENCE DESCRIPTION: SEQ ID NO:4:

```
ACAACGGGTC AGGCATGCA                                                     19
```

METHOD OF TREATMENT FOR OBSESSIVE-COMPULSIVE DISORDER

TECHNICAL FIELD OF THE INVENTION

The present invention relates generally to methods for diagnosing and treating obsessive-compulsive disorder, and to knockout mutant mouse models for testing compounds useful in said diagnosis and treatment.

BACKGROUND OF THE INVENTION

Obsessive-Compulsive Disorder (OCD) is a common and severe psychiatric condition, which affects 2–3% of the population and is characterized by anxiety-producing intrusive thoughts and performance of anxiety-reducing rituals. Several studies suggest a genetic component in the etiology of OCD, but unlike schizophrenia and bipolar illness, no genome-wide search for genes has yet been reported for this disorder. Very little is known about the pathogenesis of the disorder.

Numerous early studies involving the serotonin-specific reuptake inhibitor clomipramine led to the hypothesis that OCD may be associated with dysregulation of serotonergic neurotransmission. Indeed, serotonin reuptake inhibitors have been established as the first-line pharmacotherapy of OCD. However, approximately one-half of the patients who receive an adequate trial with these agents remain clinically unchanged. Use of dopamine antagonists to augment treatment of patients resistant to serotonin uptake inhibitors appears to be a useful approach for a subset of OCD patients, thus implicating involvement of dopaminergic pathways. However, there has heretofore been no method available to screen patients to ascertain the appropriate course of therapy. Often, it can take weeks, or even months, to establish the inappropriateness of the therapy, resulting in a continuance or worsening of the patient's condition.

Therefore, in view of the aforementioned deficiencies attendant with prior art methods of diagnosing and treating obsessive-compulsive disorder, it should be apparent that there still exists a need in the art for a method which can reliably distinguish between the populations for which therapy with dopamine antagonists is appropriate, so that early treatment can be initiated.

SUMMARY OF THE INVENTION

In accordance with the present invention, a method of identifying patients having a susceptibility to obsessive-compulsive disorder resultant from a reduced level of Catechol-O-methyltransferase (COMT) is described.

In a further embodiment, methods of treatment based upon the deficiency of COMT in patients suffering from obsessive-compulsive disorder are described.

In a particular embodiment, the present invention relates to the use of all members of the herein disclosed family of Catechol-O-methyltransferases.

The present invention also relates to a recombinant DNA molecule or cloned gene, or a degenerate variant thereof, which encodes a Catechol-O-methyltransferase; preferably a nucleic acid molecule, in particular a recombinant DNA molecule or cloned gene, encoding the Catechol-O-methyltransferase, which can be used therapeutically to treat patients suffering from obsessive-compulsive disorder.

The human and murine DNA sequences of the Catechol-O-methyltransferase of the present invention or portions thereof, may be prepared as probes to screen for complementary sequences and genomic clones in the same or alternate species. The present invention extends to probes so prepared that may be provided for screening cDNA and genomic libraries for the Catechol-O-methyltransferase. For example, the probes may be prepared with a variety of known vectors, such as the phage $\lambda$ vector. The present invention also includes the preparation of plasmids including such vectors, and the use of the DNA sequences to construct vectors expressing antisense RNA or ribozymes which would attack the mRNAs of any or all of the DNA sequences encoding Catechol-O-methyltransferase.

In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present Catechol-O-methyltransferase(s) which can be utilized to administer Catechol-O-methyltransferase to patients in need of such therapy.

The present invention naturally contemplates several means for preparation of the Catechol-O-methyltransferase, including as illustrated herein known recombinant techniques, and the invention is accordingly intended to cover such synthetic preparations within its scope. The isolation of the cDNA and amino acid sequences disclosed herein facilitates the reproduction of the Catechol-O-methyltransferase by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate Catechol-O-methyltransferase activity of target mammalian cells by potentiating the activity, or increasing the amount of Catechol-O-methyltransferase. In one instance, the test drug could be administered to an animal or cellular sample containing the Catechol-O-methyltransferase or an extract containing Catechol-O-methyltransferase to determine its effect upon the activity (modification of any appropriate substrate including neurotransmitters such as dopamine and noradrenaline) of the Catechol-O-methyltransferase, by comparison with a control.

The assay system could more importantly be adapted to identify drugs or other entities that are capable of binding to the Catechol-O-methyltransferase, in the cytoplasm or in the cellular membrane, thereby increasing or potentiating its activity. Such assay would be useful in the development of drugs that would be specific against particular cellular activity, or that would potentiate such activity, in time or in level of activity. For example, such drugs might be used to effectively treat diseases wherein COMT activity is diminished or decreased, especially in the instance of obsessive-compulsive disorder, and related disorders such as major depression dysthymia and anxiety disorders such as panic disorder, panic disorder with agoraphobia, social phobia, attention deficit hyperactivity disorder, eating disorders and Tourette's Syndrome, or to treat other pathologies.

The present invention includes an assay system which may be prepared in the form of a test kit for the quantitative analysis of the extent of the presence and/or activity of the COMT, or to identify drugs or other agents that may potentiate or increase such activity. The system or test kit may comprise a labeled component prepared by one of the radioactive and/or enzymatic techniques discussed herein, coupling a label to the COMT, their agonists and/or antagonists, and one or more additional immunochemical reagents, at least one of which is a free or immobilized ligand, capable either of binding with the labeled component, its binding partner, one of the components to be determined or their binding partner(s). The system or test kit may also comprise a polymerase chain reaction based (PCR) assay which can be used to quantify the COMT levels of a sample.

In a further embodiment, the present invention relates to certain therapeutic methods which would be based upon the activity of the COMT(s), its (or their) subunits, or active fragments thereof, or upon agents or other drugs determined to possess the same activity. A first therapeutic method is associated with the prevention of the manifestations of conditions causally related to or following from the decreased levels of COMT activity, either individually or in mixture with each other in an amount effective to prevent the development of those conditions in the host. For example, drugs may be administered to increase or potentiate COMT activity, thereby decreasing or preventing the symptoms of obsessive-compulsive disorder.

More specifically, the therapeutic method generally referred to herein could include the method for the treatment of obsessive-compulsive disorder by the administration of pharmaceutical compositions that may comprise effective enhancers of activity of COMT, or other equally effective drugs developed for instance by a drug screening assay prepared and used in accordance with a further aspect of the present invention. For example, drugs or other binding partners to the COMT, may be administered to increase the amount of, or the level of activity of COMT.

The present invention also includes a mutant mouse lacking the gene for COMT expression.

Accordingly, it is a principal object of the present invention to provide a method and associated assay system for screening patients in order to determine their susceptibility to obsessive-compulsive disorder, and to likewise select an appropriate course of therapy therefor.

It is further an object of the present invention to provide substances such as drugs, agents and the like, potentially effective in either potentiating the effects of COMT levels or increasing such levels in mammalian, especially human patients.

It is a still further object of the present invention to provide a method for the treatment of mammals to modulate the amount or activity of the COMT or subunits thereof, so as to alter the adverse consequences of diminished levels of COMT, resultant in obsessive-compulsive disorder.

It is a still further object of the present invention to provide pharmaceutical compositions for use in therapeutic methods which comprise or are based upon the COMT, its subunits, their binding partner(s), as well as molecules whose activity or production depend on COMT; or upon molecules or agents or drugs that control the production, stability and degradation, or that mimic the activities of the COMT.

It is yet another object to provide a knockout mutant mouse which lacks the COMT expression gene for use in ascertaining the effects of various test compounds upon COMT levels, and thus can be useful in the treatment of OCD and related disorders.

Other objects and advantages will become apparent to those skilled in the art from a review of the ensuing description which proceeds.

DETAILED DESCRIPTION OF THE INVENTION

In the present invention, the role of the gene for Catechol-O-methyltransferase (COMT), a key modulator of dopaminergic and noradrenergic neurotransmission, is elucidated with respect to a genetic predisposition to OCD. It can be shown that a functional allele of this gene which results in a three-to-four-fold reduction in enzyme activity, is significantly associated in a recessive manner with susceptibility of males to OCD. The mechanism underlying this association remains to be defined, but it appears to be most likely related to sexual dimorphism in COMT activity and the existence of yet largely undefined subtypes of OCD.

It has been previously described that patients with velo-cardio-facial syndrome (VCFS), carrying 22q11 microdeletions, present a number of psychiatric phenotypes including OCD, or obsessive compulsive symptoms[1, 2]. The gene for COMT a) maps in this region; b) is frequently deleted in VCFS; and c) inactivates catecholamines including the neurotransmitter dopamine. COMT therefore represents an attractive candidate for OCD from this region. A common genetic polymorphism in humans is associated with a three-to-four-fold variation in COMT enzyme activity. It has been recently shown that this variation in activity is due to a G–>A transition at codon 158 of the COMT gene that results in a valine (Val) to methionine (Met) substitution[3, 4]. The two alleles ($Val^{158}$ or High and $Met^{158}$ or Low) and the three genotypes ($Val^{158}/Val^{158}$ or High/High; $Val^{158}/Met^{158}$ or High/Low; $Met^{158}/Met^{158}$ or Low/Low) can be identified with a PCR-based restriction fragment length polymorphism analysis using the restriction enzyme NlaIII. The nucleic acid sequence for the human COMT gene in the High allele is set forth in SEQ ID NO: 1. The amino acid sequence of human COMT is set forth in SEQ ID NO:2.

The distribution of the COMT genotypes (H/H, H/L, L/L) in an OCD patient group, consisting of 73 Caucasian patients (43 males, and 30 females), and a control group consisting of 143 ethnically matched Caucasians (75 males, and 68 females), recruited from the same site as the patient group (Bethesda, Md.), and who had been evaluated and found free of any psychiatric symptoms was tested. A chi-square test of homogeneity in genotype distributions (see Table 1 below) among cases and controls and males and females was highly significant ($x^2=28.67$, 6 df, p=0.0001). Partitioning of chi-square into three components with 2 df each provided the following empirical significance levels: p=0.0206 for the "Disease" main effect, p=0.0618 for the "Sex" main effect, and p=0.0005 for the "Disease" by "Sex" interaction. Because of the high significance of the interaction term, "Disease" effects were investigated separately for males and females resulting in p=0.0002 for males and p=0.0841 for females. Clearly, association between COMT and disease is highly significant in males but not very pronounced (not formally significant) in females.

TABLE 1

Genotype Distribution at COMT gene by disease category and sex

A.

| Genotypes | OCD SAMPLE | | CONTROL SAMPLE | | | |
|---|---|---|---|---|---|---|
| | Males | Females | | Males | Females | |
| L/L | 20 (48%) | 3 (10%) | 23 | 10 (13%) | 15 (22%) | 25 |
| L/H | 17 (40%) | 19 (61%) | 36 | 44 (59%) | 26 (38%) | 70 |
| H/H | 5 (12%) | 9 (29%) | 14 | 21 (28%) | 27 (40%) | 48 |
| | 42 | 31 | 73 | 75 | 68 | 143 |

B.

| SOURCE | $x^2$ | df | 2p |
|---|---|---|---|
| Disease | 7.76 | 2 | 0.0206 |
| Sex | 5.57 | 2 | 0.0618 |
| DxS | 15.34 | 2 | 0.0005 |
| Total | 28.67 | 6 | 0.0001 |

C. Effect of disease by:

| | | |
|---|---|---|
| Males: (n = 117) | $x^2 = 17.19$ | 2p = 0.0002 |
| Females: (n = 99) | $x^2 = 4.95$ | 2p = 0.0841 |

Odds ratios (approximate relative risks) in males relative to one genotype over another were computed. Results in Table 2 below show that genotypes H/L and H/H do not differ significantly from each other in their effect as risk factors for disease, while the L/L/ genotype appears to be a strong risk factor. Thus, the COMT gene appears to act in a recessive manner. Pooling genotypes H/L and H/H leads to an approximate relative risk of 5.91 for genotype L/L versus non-L/L (last line in Table 2). Analogous results shown below in Table 3 were obtained when analyses were carried out for alleles rather than genotypes, that is, association is essentially confined to males.

TABLE 2

Odds Ratio (approximate relative risk) for disease with genotype as a risk factor (confidence interval computed as logit limits)

| Genotype | Odds ratio | 95% confidence interval |
|---|---|---|
| L/L vs. H/L | 5.18 | (2.02, 13.29) |
| H/L vs. H/H | 1.62 | (0.53, 5.00) |
| L/L vs. H/H | 8.40 | (2.44, 28.91) |
| L/L vs. (H/L and H/H) | 5.91 | (2.40, 14.53) |

TABLE 3

Analysis of Allelic Association of the COMT High and Low Activity Polymorphism
A. Allele Distribution at COMT gene by Disease and Sex

| Alleles | OCD SAMPLE | | CONTROL SAMPLE | |
|---|---|---|---|---|
| | Males | Females | Males | Females |
| L | 57 (0.68) | 25 (0.40) | 64 (0.43) | 61 (0.42) |
| H | 27 (0.32) | 37 (0.60) | 86 (0.57) | 85 (0.58) |

B. Chi-Square Test of Homogeneity in Allele Distribution

| SOURCE | $x^2$ | df | 2p |
|---|---|---|---|
| Disease | 7.84 | 1 | 0.0052 |
| Sex | 5.03 | 1 | 0.0250 |
| DxS | 5.89 | 1 | 0.0152 |
| Total | 18.76 | 3 | 0.0003 |

C. Effect of Disease by Sex

| | | |
|---|---|---|
| Males: | $x^2 = 13.68$ | 2p = 0.0002 |
| Females: | $x^2 = 0.01$ | 2p = 0.9097 |

An association between a genetic polymorphism and a phenotype can arise either because of a direct relationship between the gene and the disease phenotype, or because subpopulations that have different frequencies of the polymorphism also happen to differ in average susceptibility to the disease (population stratification). However, the strength and the sex-specificity of the association described here make it unlikely that it is the result of a population stratification effect. Previous analysis of the distribution of the COMT alleles and genotypes in patients with schizophrenia (another psychiatric condition associated with 22q11 deletions) did not reveal significant differences[3]. In addition, an extensive mutational analysis of this gene in 156 schizophrenic patients failed to reveal any mutations (Karayiorgou et al., submitted).

As mentioned above, use of dopamine antagonists in the regimens of patients resistant to serotonin reuptake inhibitors appears to be an approach of choice for a subset of OCD patients, most notably, but not exclusively, for the ones with a comorbid chronic tic disorder (e.g., Tourette's syndrome) and possibly for those with concurrent psychotic spectrum disorders[5]. In that respect it is interesting to note a trend for an increased frequently of comorbid tic disorders among males with the L/L genotype than among males with the non-L/L genotype in our sample [odds ratio 2.24 (0.56, 8.91)].

No systematic studies have addressed the issue of sex-specific differences of COMT activity in humans. A limited number of studies in other species suggest that COMT activity can be affected epigenetically by estrogen (decreased) and by the process of sexual differentiation of the brain[6]. Along these lines, it has also been suggested that estrogens could directly modulate neurotransmission through their conversion into catecholestrogens (CE)[7, 8], which are known to be powerful inhibitors of COMT.

These results, along with the drug response data mentioned above, suggest that both the 5-HT and dopamine systems (and more specifically COMT) are involved in the pathophysiology of OCD and can be targeted in the treatment of this disease.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "Catechol-O-methyltransferase","COMT", and any variants not specifically listed, may be used herein interchangeably, and as used throughout the present application and claims refer to proteinaceous material including single or multiple proteins, and extends to those proteins having the amino acid sequence data described in Lundstrom et al., *DNA and Cell Biology*, 10:3, 181–189 (1991). Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552–59 (1969), abbreviations for amino acid residues are shown in the following Table of Correspondence:

| TABLE OF CORRESPONDENCE | | |
|---|---|---|
| SYMBOL | | AMINO ACID |
| 1-Letter | 3-Letter | |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of aminoterminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, CDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding Catechol-O-methyltransferase which code for a Catechol-O-methyltransferase having the same amino acid sequence, but which are degenerate thereto. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the DNA COMT that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups

Alanine
Valine
Leucine
Isoleucine
Proline
Phenylalanine

Tryptophan
Methionine

Amino Acids with Uncharged Polar R Groups

Glycine
Serine
Threonine
Cysteine
Tyrosine
Asparagine
Glutamine

Amino Acids with Charged Polar R Groups
(Negatively Charged at Ph 6.0)

Aspartic acid
Glutamic acid

Basic Amino Acids (Positively Charged at pH 6.0)

Lysine
Arginine
Histidine (at pH 6.0)

Another grouping may be those amino acids with phenyl groups:
Phenylalanine
Tryptophan
Tyrosine Another grouping may be according to molecular weight (i.e., size of R groups):

| Amino Acid | Weight |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to treat, and preferably increase by at least about 30 percent, more preferably by at least 50 percent, most preferably by at least 90 percent, a clinically significant change in obsessive-compulsive disorder due to the lowered levels of COMT.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10°–20° C. below the predicted or determined $T_m$ with washes of higher stringency, if desired.

In its primary aspect, the present invention concerns the identification of a patient population having reduced levels of COMT and a high susceptibility to obsessive-compulsive disorder.

In a particular embodiment, the present invention relates to all members of the herein disclosed COMT.

As stated above, the present invention also relates to a recombinant DNA molecule or cloned gene, or a degenerate variant thereof, which encodes a COMT, or a fragment thereof; preferably a nucleic acid molecule, in particular a recombinant DNA molecule or cloned gene, encoding the COMT, which can be used to therapeutically administer COMT to a patient in need of such therapy.

The possibilities both diagnostic and therapeutic that are raised by the existence of the relationship between COMT levels and obsessive-compulsive disorder, derive from the fact that the low levels of COMT appear to participate in direct and causal protein-protein interaction which results in the exhibition of the obsessive-compulsive disorder symptoms. As suggested earlier and elaborated further on herein, the present invention contemplates pharmaceutical intervention in the cascade of reactions in which the levels of COMT is implicated, to moderate or abate the symptoms of obsessive-compulsive disorder.

In the instances where insufficient levels of COMT are present, such could be remedied by the introduction of additional quantities of the COMT or its chemical or pharmaceutical cognates, analogs, fragments and the like.

As discussed earlier, the COMT or their binding partners, as well as molecules whose activity or production depends on COMT, or other molecules or ligands or agents exhibiting mimicry of the COMT or control over its production and activity, may be prepared in pharmaceutical compositions, with a suitable carrier and at a strength effective for administration by various means to a patient experiencing the symptoms of obsessive-compulsive disorder. A variety of administrative techniques may be utilized, among them parenteral techniques such as subcutaneous, intravenous and intraperitoneal injections, catheterizations and the like. Average quantities of the COMT or their subunits may vary and in particular should be based upon the recommendations and prescription of a qualified physician or veterinarian.

Also, antibodies including both polyclonal and monoclonal antibodies, and drugs that modulate the production or activity of the COMT and/or their subunits may possess certain diagnostic applications and may for example, be utilized for the purpose of detecting and/or measuring the susceptibility to or presence of obsessive-compulsive disorder. For example, the COMT or its subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic the activity(ies) of the COMT of the invention may be discovered or synthesized, and may be used in diagnostic and/or therapeutic protocols.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against COMT can be screened for various properties; i.e., isotope, epitope, affinity, etc. Of particular interest are monoclonal antibodies that neutralize the activity of the COMT or its subunits. Such monoclonals can be readily identified in COMT activity assays. High affinity antibodies are also useful when immunoaffinity purification of native or recombinant COMT is possible.

Preferably, the anti-COMT antibody used in the diagnostic methods of this invention is an affinity purified polyclonal antibody. More preferably, the antibody is a monoclonal antibody (mAb). In addition, it is preferable for the anti-antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a COMT/protein, such as an anti- COMT antibody, preferably an affinity-purified polyclonal antibody, and more preferably a mAb. In addition, it is preferable for the anti-COMT antibody molecules used herein be in the form of Fab, Fab', F(ab')$_2$ or F(v) portions or whole antibody molecules. As previously discussed, patients capable of benefiting from this method include those suffering from OCD and related disorders such as major depression, and dysthymia, and other anxiety disorders (i.e., panic disorder, panic disorder with agoraphobia, social phobia, attention deficit hyperactivity disorder), as well as eating disorders and Tourette's Syndrome. Methods for isolating the COMT and inducing anti-COMT antibodies and for determining and optimizing the ability of anti-COMT antibodies to assist in the examination of the target cells are all well-known in the art.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in Antibodies - A Laboratory Manual, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a COMT-binding portion thereof, or COMT, or an origin-specific DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present COMT and their ability to inhibit specified COMT activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/l glucose, 20 mm glutamine, and 20% fetal calf serum. An exemplary inbred mouse strain is the Balb/c.

Methods for producing monoclonal anti-COMT antibodies are also well-known in the art. See Niman et al., Proc. Natl. Acad. Sci. USA, 80:4949–4953 (1983). Typically, the present COMT or a peptide analog is used either alone or conjugated to an immunogenic carrier, as the immunogen in the before described procedure for producing anti-COMT monoclonal antibodies. The hybridomas are screened for the ability to produce an antibody that immunoreacts with the COMT peptide analog and the present COMT.

The present invention further contemplates therapeutic compositions useful in practicing the therapeutic methods of this invention. A subject therapeutic composition includes, in admixture, a pharmaceutically acceptable excipient (carrier) and one or more of a COMT, polypeptide analog thereof or fragment thereof, as described herein as an active ingredient.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, and the severity of the disease under treatment. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration.

The therapeutic compositions may further include an effective amount of a dopamine antagonist in combination with the COMT or COMT agonist which is an agent capable of mimicking the activity of COMT. Representative of such dopamine antagonists are those such as haloperidol and pimozide. Exemplary formulations are given below:

| Formulations | |
|---|---|
| Ingredient | mg/ml |
| Intravenous Formulation I | |
| COMT/COMT agonist | 10.0 |
| dextrose USP | 45.0 |
| sodium bisulfite USP | 3.2 |
| edetate disodium USP | 0.1 |
| water for injection q.s.a.d. | 1.0 ml |
| Intravenous Formulation II | |
| COMT/COMT agonist | 5.0 |
| haloperidol | 5.0 |
| sodium bisulfite USP | 3.2 |
| disodium edetate USP | 0.1 |
| water for injection q.s.a.d. | 1.0 ml |

As used herein, "pg" means picogram, "ng" means nanogram, "ug" or "Ag" mean microgram, "mg" means milligram, "ul" or "µl" mean microliter, "ml" means milliliter, "l" means liter.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host.

Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, Rl.1, B–W and L–M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

It is further intended that COMT analogs may be prepared from nucleotide sequences of the protein complex/subunit derived within the scope of the present invention. Analogs, such as fragments, may be produced, for example, by pepsin digestion of COMT material. Other analogs, such as muteins, can be produced by standard site-directed mutagenesis of COMT coding sequences. Analogs exhibiting "COMT-activity" such as small molecules, whether functioning as promoters or inhibitors, may be identified by known in vivo and/or in vitro assays.

As mentioned above, a DNA sequence encoding COMT can be prepared synthetically rather than cloned. The DNA sequence can be designed with the appropriate codons for the COMT amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express COMT analogs or "muteins". Alternatively, DNA encoding muteins can be made by site-directed mutagenesis of native COMT genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

The present invention also relates to a variety of diagnostic applications, including methods for detecting a susceptibility to, or the presence of, obsessive-compulsive disorder, by reference to the amount of COMT present in a patient when compared to controls. As mentioned earlier, the COMT can be used to produce antibodies to itself by a variety of known techniques, and such antibodies could then be isolated and utilized as in tests for the presence of particular COMT activity in suspect target cells.

As described in detail above, antibody(ies) to the COMT can be produced and isolated by standard methods including the well known hybridoma techniques. For convenience, the antibody(ies) to the COMT will be referred to herein as $Ab_1$ and antibody(ies) raised in another species as $Ab_2$.

The presence of COMT in cells can be ascertained by the usual immunological procedures applicable to such determinations. A number of useful procedures are known. Three such procedures which are especially useful utilize either the COMT labeled with a detectable label, antibody $Ab_1$ labeled with a detectable label, or antibody $Ab_2$ labeled with a detectable label. The procedures may be summarized by the following equations wherein the asterisk indicates that the particle is labeled, and "COMT" stands for the Catechol-O-methyltransferase:

A. COMT*+Ab1=COMT*Ab$_1$
B. COMT+Ab*=COMTAb$_1$*
C. COMT+Ab$_1$+Ab$_2$*=COMTAb$_1$Ab$_2$*

The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure.

In each instance, the COMT forms complexes with one or more antibody(ies) or binding partners and one member of the complex is labeled with a detectable label. The fact that a complex has formed and, if desired, the amount thereof, can be determined by known methods applicable to the detection of labels.

It will be seen from the above, that a characteristic property of Ab$_2$ is that it will react with Ab$_1$. This is because Ab$_1$ raised in one mammalian species has been used in another species as an antigen to raise the antibody Ab$_2$. For example, Ab$_2$ may be raised in goats using rabbit antibodies as antigens. Ab$_2$ therefore would be anti-rabbit antibody raised in goats. For purposes of this description and claims, Ab$_1$ will be referred to as a primary or anti-COMT antibody, and Ab$_2$ will be referred to as a secondary or anti-Ab$_1$ antibody.

The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The COMT or its binding partner(s) can also be labeled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

A particular assay system developed and utilized in accordance with the present invention, is known as a receptor assay. In a receptor assay, the material to be assayed is appropriately labeled and then certain cellular test colonies are inoculated with a quantity of both the labeled and unlabeled material after which binding studies are conducted to determine the extent to which the labeled material binds to the cell receptors. In this way, differences in affinity between materials can be ascertained.

Accordingly, a purified quantity of the COMT may be radiolabeled and combined, for example, with antibodies or other inhibitors thereto, after which binding studies would be carried out. Solutions would then be prepared that contain various quantities of labeled and unlabeled uncombined COMT, and cell samples would then be inoculated and thereafter incubated. The resulting cell monolayers are then washed, solubilized and then counted in a gamma counter for a length of time sufficient to yield a standard error of <5%. These data are then subjected to Scatchard analysis after which observations and conclusions regarding material activity can be drawn. While the foregoing is exemplary, it illustrates the manner in which a receptor assay may be performed and utilized, in the instance where the cellular binding ability of the assayed material may serve as a distinguishing characteristic.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

Alternatively, a PCR assay can be utilized. For example, for detection of the NlaIII polymorphism in codon 158, the following primers were used: F: 5' TCACCATCGAGAT-CAACCCC (SEQ ID NO:3), R: 5' ACAACGGGTCAG-GCATGCA (SEQ ID NO:4). PCR was performed with the thermostable enzyme Taq polymerase (1.5 u/sample) (AmpliTaq, Perkin Elmer Cetus) and a programmable PCR apparatus (MJ Research, Inc.). Target sequences were amplified in a 10 μl reaction mixture containing 100 ng of genomic DNA in 75 mM KCl, 10 mM Tris-HCl (pH 9.2), 1.5 mM MgCl$_2$, 5 pmol of each primer, 100 mM of each dNTP (dATP, dCTP, dGTP, dTTP) and $^{32}$P-dCTP. Amplification was as follows: 94° C.×3 min. (1X), 94° C.×30 sec./64° C.×1 min./72° C.×1 min. (35X), 72° C.×7 min. (1X), 4° C.×5 min. 5μ of the amplified product was digested with Nla in a 10 μl reaction volume, according to the manufacturer's specifications. The digested product was diluted 1:1 with formamide-dye, denatured at 95° C.×5 min., and electrophoresed in a 6% 1XTBE polyacrylamide gel, at 1,200 V×2.5 h at room temperature. Gels were dried and signal was detected by overnight autoradiography without an intensifying screen.

In addition, an activity assay, such as described by Weinshilboum and Raymond (1977), can be utilized to determine the presence or absence of COMT activity.

In a further embodiment of this invention, commercial test kits suitable for use by a medical specialist may be prepared to determine the presence or absence of predetermined COMT activity or predetermined COMT activity capability in target patient populations. In accordance with the testing techniques discussed above, one class of such kits will contain at least the labeled COMT or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Another class of such kits may also include PCR reagents, such as oligonucleotide primers, enzymes, gel matrixes, buffers, etc.

Accordingly, a test kit may be prepared for the diagnosis or detection of a susceptibility to obsessive-compulsive disorder which comprises measurement of the levels of COMT activity, comprising:

(a) a predetermined amount of at least one labeled immunochemically reactive component obtained by the direct or indirect attachment of the present COMT factor or a specific binding partner thereto, to a detectable label;

(b) other reagents; and (c) directions, including comparison levels of COMT, for use of said kit.

An alternate kit for measuring the levels of COMT activity may comprise PCR reagents, such as oligonucleotide primers, enzymes, gel matrixes, buffers, directions, including comparison levels of COMT, for use of said kit. A still further alternate can utilize reagents for measuring the levels of COMT activity as described by Weinshiboum and Raymond (1977); and directions, including comparison levels of COMT, for use of said kit.

More specifically, the diagnostic test kit may comprise:

(a) a known amount of the COMT as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions, including comparison levels of COMT, for use of said kit.

In a further variation, the test kit may be prepared and used for the purposes stated above, which operates according to a predetermined protocol (e.g. "competitive," "sandwich," "double antibody," etc.), and comprises:

(a) a labeled component which has been obtained by coupling the COMT to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the COMT and a specific binding partner thereto.

In accordance with the above, an assay system for screening potential drugs effective to increase the levels of, or the activity of, the COMT may be prepared. The COMT may be introduced into a test system, and the prospective drug may also be introduced into the resulting cell culture, and the culture thereafter examined to observe any changes in the COMT activity of the cells, due either to the addition of the prospective drug alone, or due to the effect of added quantities of the known COMT.

Figure 1:
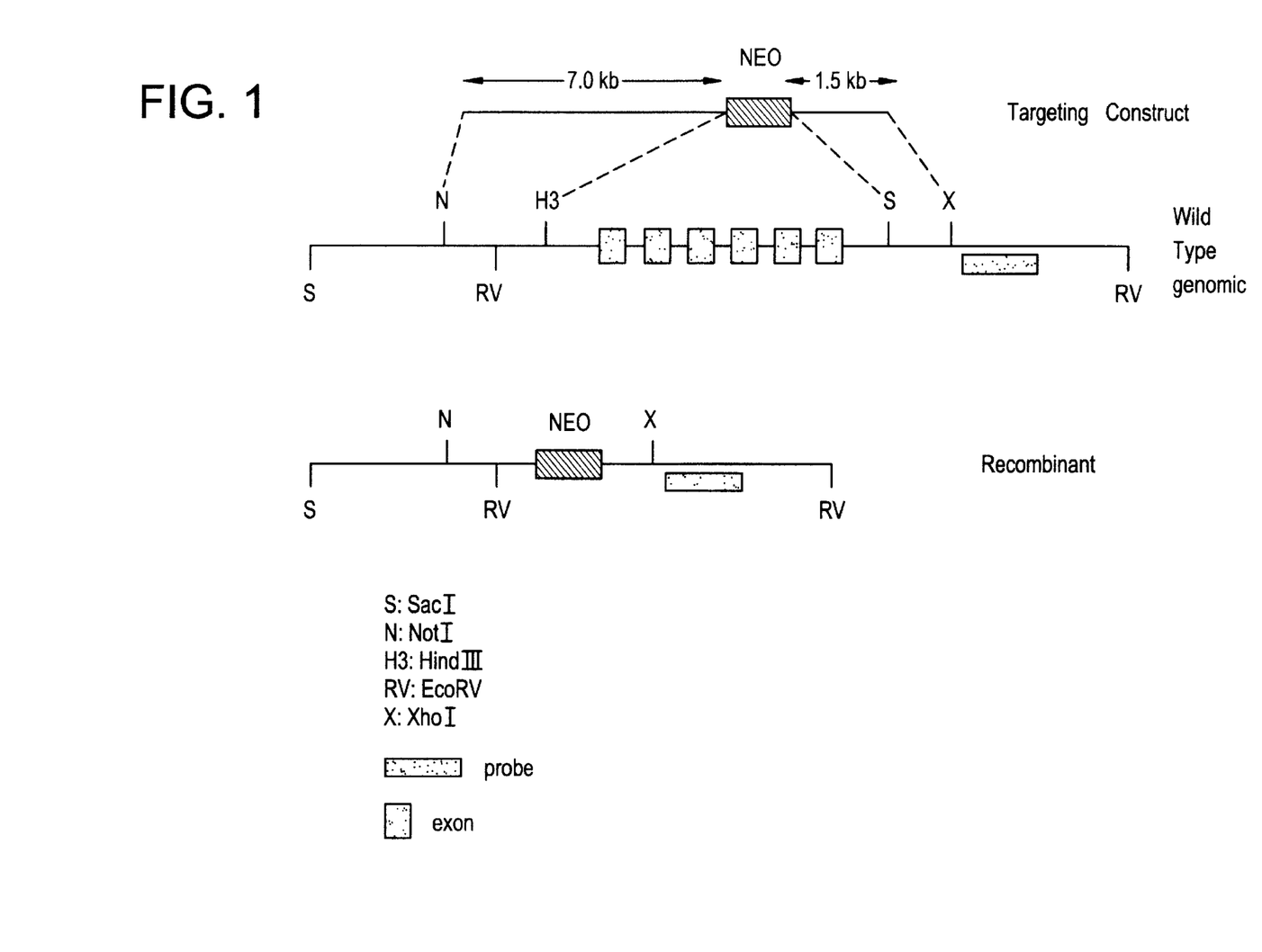
FIG. 1 is a schematic drawing of the mouse gene for COMT and the comparison knockout mouse gene lacking COMT.

In a further embodiment of this invention, a mouse model has been developed to facilitate drug development and testing. The entire coding region of the mouse COMT has been deleted using conventional gene targeting approaches in ES cells (See FIG. 1). The introduced mutation was transmitted through the germline, and mice homozygous for the deletion have been obtained. The expression of the gene for COMT and the activity of the COMT enzyme was examined in these mice.

Figure 2:
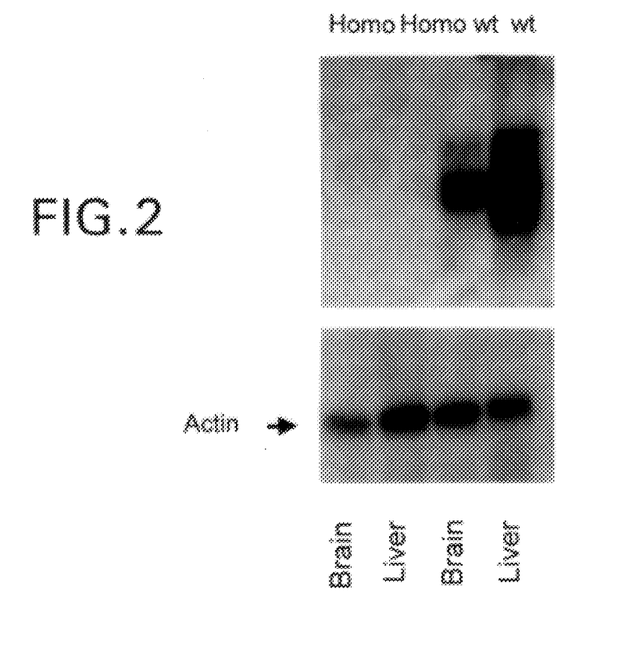
FIG. 2 is a Northern analysis of mRNA extracted from the liver and brain of the homozygote animals as well as from wild type controls, showing the elimination of the expression of the COMT gene in the knockout mouse.

Northern analysis, using total mRNA extracted from the liver and the brain of the homozygote animals as well as from wild type control animals, demonstrated the anticipated elimination in the expression of this gene in the mutant animals (See FIG. 2).

One of the major metabolic pathways COMT participates in, involves methylation and inactivation of the released dopamine as follows:

Dopamine - - - (MAO) - - - - > 3,4-dihydroxyphenylacetaldehyde - - - (ALDEHYDE DEHYDROGENASE) - - - - > DOPAC - - - (COMT) - - - - > HVA

TABLE 5

|  |  | DOPAC (Avg. Values) | HVA (Avg. Values) |
|---|---|---|---|
| Striatum | Control (wt) Animals | 7.5 | 15.1 |
|  | Knock-Out Animals | 20.2 | 1.08* |
| Frontal Cortex | Control (wt) Animals | 0.9 | 1.97 |
|  | Knock-Out Animals | 7.7 | 0.47 |
| Hypothalamus | Control (wt) Animals | 2.48 | 5.3 |
|  | Knock-Out Animals | 9.2 | 0.9* |

*Sign. Diff. by T-Test

The behavior of the mutant animals (especially in reference to behavioral traits that are known to be affected in OCD, such as anxiety, stereotypic movement, etc. are useful for analysis in that they can be administered test compounds suspected of possessing potential therapeutic utility to ascertain their effects upon the behavioral traits.

Further, the effect of the COMT gene deletion on certain neurotransmitter systems in the brain, including the serotonin system that is known to be affected in OCD can be analyzed, and test compounds administered to ascertain their effects thereon. Preliminary results suggest that the levels of serotonin are affected in the mutant animals.

Other mouse strains can also be used to identify strain specific modifiers of a COMT associated phenotype.

A mouse strain where the low activity form of the human COMT gene can be introduced as a transgene in a COMT(−) background. These animals can be also utilized in testing compounds that could potentially increase COMT activity and stability.

The knockout mutant mice produced in accordance with the present invention are thus useful for determining the obsessive-compulsive disorder-related pharmacological activity of a compound due to their phenotype that comprises a complete or diminished ability to express COMT.

This present invention thus also provides a method of selecting a therapeutic agent for possible use in the treatment of OCD which comprises:

A. administering a potential therapeutic agent to a knock-out mouse having a phenotype that comprises a complete or diminished ability to express COMT;

B. measuring the effects of the agent vis-à-vis the behavioral effects exhibited by said mouse;

C. comparing said effects of the agent to those of a control; and

D. selecting a therapeutic agent by comparing the test responses.

The following is a list of documents related to the above disclosure and particularly to the experimental procedures and discussions. The documents should be considered as incorporated by reference in their entirety.

1. Karayiorgou, M. et al. Schizophrenia susceptibility associated with interstitial deletions of chromosome 22q11. *Proc. Natl. Acad. Sci. USA* 92, 7612–7616 (1995).

2. Pulver, A. E. et al. Psychotic illness in patients diagnosed with velo-cardio-facial syndrome and their relatives. *J. Nerv. Mental Disease* 182, 476–478 (1994).

3. Karayiorgou, M. et al. Genotype and Phenotype Analysis at the 22q11 Schizophrenia Susceptibility Locus. (in press, *Cold Spring Harbor Symposia on Quantitative Biology, Vol. LXI*).

4. Lachman, H. M., Papolos, D. F., Saito, T., Yu, Y-M, Szumlanski, C. L. & Weinshilboum, R. M. Human catechol-O-methyltransferase pharmacogenetics: description of a functional polymorphism and its potential application to neuropsychiatric disorders. Pharmacogenetics 6, 243–250 (1996).

5. McDougle, C. J., Goodman, W. K. & Price, L. H. Dopamine antagonists in tic-related and psychotic spectrum obsessive compulsive disorder. [Review]. *J. Clin. Psych.* 55 Suppl, 24–31 (1994).

6. Balthazart, J., Foidart, A., Absil, P. & Harada, N. Effects of testosterone and its metabolites on aromatase-immunoreactive cells in the quail brain: relationship with the activation of male reproductive behavior. *J. Steroid Biochem. Mol. Biol.* 56, 185–200 (1996).

7. Ladosky, W. & Schneider, H. T. Changes in hypothalamic catechol-O-methyltransferase during sexual differentiation of the brain. *Br. J. Med. Biol. Res.* 14, 409–413 (1981).

8. Cohn, C. K. & Axelrod, J. The effect of estradiol on catechol-O-methyltransferase activity in rat liver. *Life Sci.* 10, 1351–1354 (1971).

9. Weinshilboum, R. M. and Raymond, F. A., Inheritance of Row Erythrocyte Catechol-O-Methyltransferase Activity in Man. *Am. J. Hum. Genet.* 29, 125–135 (1977).

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

---

What is claimed is:

1. A method of detecting a susceptibility to, or the presence of, obsessive-compulsive disorder in Caucasian males which comprises:

a) obtain a Catechol-O-methyltransferase (COMT)-containing sample from a Caucasian male;

b) measure the level of COMT activity in said sample; and compare said level of enzymatic activity to a standard, whereby reduced enzymatic activity levels indicate the susceptibility to, or the presence of, obsessive-compulsive disorder in Caucasian males.

2. A method for detecting a susceptibility to, or the presence of, obsessive-compulsive disorder in Caucasian males wherein said method comprises:

a) obtain a nucleic acid-containing sample from a Caucasian male;

b) determine the presence, or absence, of a single base substitution at codon 158 of each allele of the COMT gene wherein a substitution of G to A in either, or both alleles, is indicative of a susceptibility to, or the presence of, obsessive-compulsive disorder in said Caucasian male.

3. A test kit to facilitate diagnosis and treatment of obsessive-compulsive disorder in Caucasian males, comprising:

a) oligonucleotide primers of at least 15 nucleotides wherein said primers are fully complementary to the nucleotide residue sequence adjacent to codon 158 of the COMT gene;

other reagents; and directions for use of said kit.

4. The kit of claim 1 wherein said primers are SEQ ID NO:3 and SEQ ID NO:4.

5. The kit of claim 1 wherein said kit further comprises restriction endonuclease NlalII.

* * * * *

UNITED STATES PATENT AND TRADEMARK OFFICE
CERTIFICATE OF CORRECTION

PATENT NO. : 5,863,734
DATED : January 26, 1999
INVENTOR(S) : Karayiorgou et al.

It is certified that error appears in the above-identified patent and that said Letters Patent is hereby corrected as shown below:

Col. 30, line 55, after "claim" remove "1"
and insert therefor --3--.

Col. 30, line 57, after "claim" remove "1"
and insert therefor --3--.

Signed and Sealed this

Twentieth Day of July, 1999

Attest:

Q. TODD DICKINSON

Attesting Officer

Acting Commissioner of Patents and Trademarks